(12) United States Patent
Mazur et al.

(10) Patent No.: US 11,499,865 B2
(45) Date of Patent: Nov. 15, 2022

(54) ENVIRONMENTAL ACOUSTIC DOSIMETRY WITH WATER EVENT DETECTION

(71) Applicant: Apple Inc., Cupertino, CA (US)

(72) Inventors: Jakub Mazur, Santa Clara, CA (US); Tyrone T. Chen, San Jose, CA (US); Hang Zhang, Santa Clara, CA (US)

(73) Assignee: APPLE INC., Cupertino, CA (US)

( * ) Notice: Subject to any disclaimer, the term of this patent is extended or adjusted under 35 U.S.C. 154(b) by 275 days.

(21) Appl. No.: 16/872,103

(22) Filed: May 11, 2020

(65) Prior Publication Data

US 2020/0378824 A1 Dec. 3, 2020

Related U.S. Application Data

(60) Provisional application No. 62/855,956, filed on Jun. 1, 2019.

(51) Int. Cl.
*G01H 3/14* (2006.01)
*H03G 11/00* (2006.01)
(Continued)

(52) U.S. Cl.
CPC .......... *G01H 3/14* (2013.01); *A61B 5/12* (2013.01); *A61B 5/6817* (2013.01); *G01H 11/06* (2013.01);
(Continued)

(58) Field of Classification Search
CPC ....... A61B 5/12; A61B 5/6817; A61B 5/6806; A61F 11/06; A61F 11/08; B01L 3/502761; G01H 3/14; G01H 11/06; G01T 7/125; G01T 7/02; G06F 1/163; G06F 3/011; G06F 3/016; G06F 3/041; G06F 3/0446; G06F 3/0488; G06F 3/165; G06F 16/61;
(Continued)

(56) References Cited

U.S. PATENT DOCUMENTS 9,609,449 B1  3/2017  Maenpaa
2002/0076057 A1*  6/2002  Voix .................. A61F 11/08
                                                          381/328

(Continued)

FOREIGN PATENT DOCUMENTS

| CN | 104571849 | 4/2015 |
| CN | 109375497 | 2/2019 |
| JP | 2001-124621 | 5/2001 |

OTHER PUBLICATIONS

Notice of Preliminary Rejection for Korean Application No. 10-2020-0064175 dated Sep. 23, 2021, 10 pages.
(Continued)

*Primary Examiner* — Gerald Gauthier
(74) *Attorney, Agent, or Firm* — Womble Bond Dickinson (US) LLP

(57) ABSTRACT

In-ear sound pressure level, SPL, is determined that is caused by output audio being converted into sound by a headset worn by a user. The in-ear SPL is converted into a sound sample having units that are suitable for evaluating sound noise exposure. These operations are repeated to produce a sequence of sound samples during playback. This sequence of sound samples is then written to a secure database. Access to the database is authorized by the user. Other aspects are also described and claimed.

20 Claims, 7 Drawing Sheets

(51) Int. Cl.
*A61B 5/12* (2006.01)
*A61B 5/00* (2006.01)
*G06F 16/61* (2019.01)
*G01H 11/06* (2006.01)
*G06F 3/16* (2006.01)
*G06V 10/44* (2022.01)

(52) U.S. Cl.
CPC .............. *G06F 3/165* (2013.01); *G06F 16/61* (2019.01); *G06V 10/44* (2022.01); *H03G 11/008* (2013.01); *H04R 2460/15* (2013.01)

(58) Field of Classification Search
CPC .. G06F 16/636; G06F 16/65; G06F 3/041662; G06F 16/686; G06V 10/44; G10L 15/22; G10L 25/06; G10L 15/51; G16H 30/40; H03G 3/3005; H03G 11/008; H04R 1/1016; H04R 1/1041; H04R 2201/107; H04R 2460/15; H04R 2499/11; H04R 2499/15; H04R 29/00; H04R 29/004; H04R 29/008; H04R 19/005; G02B 27/017; G08B 7/06; H04W 4/023
USPC ........ 73/647; 340/540; 345/173; 381/56, 59, 381/71, 6, 72, 107, 60
See application file for complete search history.

(56) References Cited

U.S. PATENT DOCUMENTS

| | | | |
|---|---|---|---|
| 2007/0186656 A1* | 8/2007 | Goldberg | G01H 3/14 73/647 |
| 2007/0214893 A1 | 9/2007 | Killion | |
| 2008/0037797 A1* | 2/2008 | Goldstein | H04R 1/1016 381/328 |
| 2008/0118087 A1* | 5/2008 | Cheyne | G01H 3/14 381/107 |
| 2008/0159547 A1 | 7/2008 | Schuler et al. | |
| 2008/0205660 A1 | 8/2008 | Goldstein | |
| 2010/0046767 A1* | 2/2010 | Bayley | G01H 3/14 381/59 |
| 2010/0135502 A1 | 6/2010 | Keady et al. | |
| 2010/0141439 A1* | 6/2010 | Lunner | G01H 3/14 340/540 |
| 2012/0051555 A1 | 3/2012 | Schevciw et al. | |
| 2013/0094658 A1 | 4/2013 | Holler | |
| 2014/0253478 A1* | 9/2014 | Jeong | G06F 3/041 345/173 |
| 2014/0294191 A1* | 10/2014 | Parkins | A61F 11/06 381/72 |
| 2015/0139432 A1* | 5/2015 | Barwicz | H04R 29/00 381/56 |
| 2015/0287421 A1 | 10/2015 | Benway et al. | |
| 2016/0150333 A1* | 5/2016 | Goldstein | G10L 15/22 381/56 |
| 2017/0178628 A1 | 6/2017 | Macours et al. | |
| 2017/0374444 A1 | 12/2017 | McNeill et al. | |
| 2018/0059866 A1* | 3/2018 | Drake | G06F 3/0488 |
| 2018/0307374 A1 | 10/2018 | Shah et al. | |
| 2018/0335872 A1* | 11/2018 | Vinje | G06F 3/0446 |
| 2018/0359555 A1 | 12/2018 | Jenkins et al. | |
| 2019/0082044 A1* | 3/2019 | Melendez | H04W 4/023 |
| 2019/0154497 A1* | 5/2019 | Goldstein | G01H 3/14 |
| 2019/0347501 A1* | 11/2019 | Kim | G06F 3/011 |
| 2020/0004016 A1* | 1/2020 | Gross | G02B 27/017 |
| 2020/0064494 A1* | 2/2020 | Trost | G01T 7/125 |
| 2020/0077892 A1* | 3/2020 | Tran | A61B 5/6806 |
| 2020/0253667 A1* | 8/2020 | Fouts | G16H 30/40 |
| 2020/0261909 A1* | 8/2020 | Auner | B01L 3/502761 |
| 2020/0378824 A1* | 12/2020 | Mazur | G01H 3/14 |
| 2020/0379717 A1* | 12/2020 | Mazur | A61B 5/12 |
| 2020/0379718 A1* | 12/2020 | Mazur | G06F 3/165 |
| 2021/0358515 A1* | 11/2021 | Williams | G10L 25/06 |
| 2022/0092960 A1* | 3/2022 | Arumugam | G08B 7/06 |
| 2022/0212036 A1* | 7/2022 | Naqa | A61N 5/1039 |

OTHER PUBLICATIONS

Office Action for U.S. Appl. No. 16/872,120 dated May 13, 2021, 25 pages.
Office Action for U.S. Appl. No. 16/872,084 dated Mar. 18, 2021, 17 pages.
Notice of Final Rejection for Korean Application No. 10-2020-0064175 dated Jan. 10, 2022, 6 pages.
U.S. Appl. No. 62/897,118, filed Sep. 6, 2019.
Office Action for Chinese Application No. 202010482766.3 dated May 27, 2021, 21 pages.

* cited by examiner

ENVIRONMENTAL ACOUSTIC DOSIMETRY WITH WATER EVENT DETECTION

This non-provisional patent application claims the benefit of the earlier filing date of provisional application No. 62/855,956 filed Jun. 1, 2019.

FIELD

An aspect of the disclosure here relates to digital signal processing techniques for monitoring a user's environmental sound energy using a water event detector to improve accuracy.

BACKGROUND

Consumer electronic headsets have become increasingly popular with users, because they reproduce media such as a music, podcasts and movie sound tracks with high fidelity while at the same time not disturbing others who are nearby. While the listening experience with a headset is enjoyable, and the maximum sound output of a headset is limited in accordance with hearing health safety standards, there is still a need to monitor the headset's sound output over relatively long periods of time such as days and weeks, as part of personal hearing health monitoring that aims to avoid long term exposure to loud sounds.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
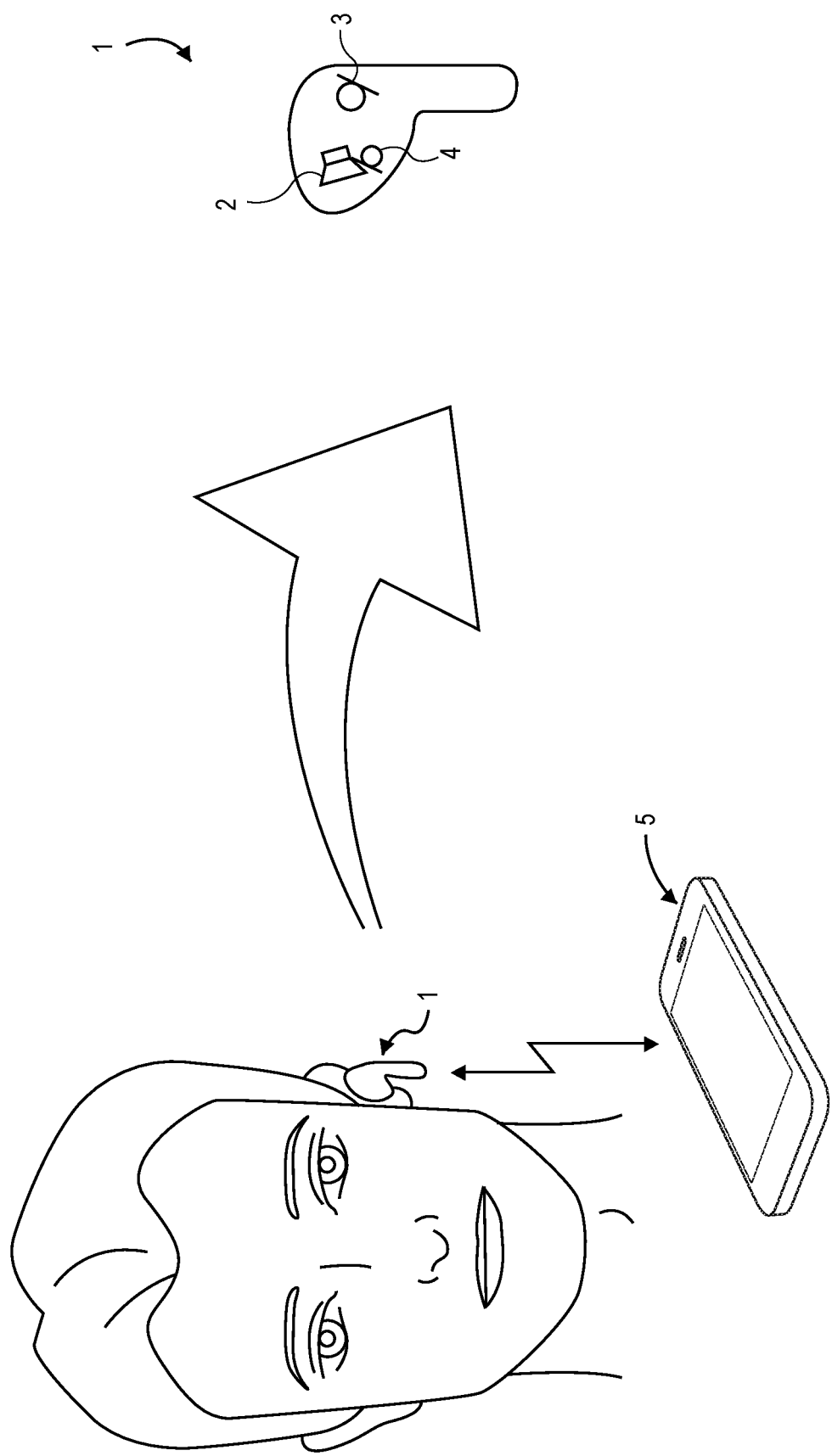
FIG. 1 shows an example audio system having a headset and an audio source device.

FIG. 1 shows an example of an against-the-ear audio device 1 that is part of an audio system in which an audio signal processing method for acoustic dosimetry of sound produce by the against-the-ear audio device 1 can be implemented. The against-the-ear audio device 1 shown is an in-ear earbud (in-ear headphone which may be a sealing type that has a flexible tip, or it may be a non-sealing type also referred to as loose fitting.) The against-the-ear audio device 1 may be one of two headphones (left and right) that make up a headset. The methods described below can be implemented for one or both of the headphones that make up a headset. Alternatives (not shown) to the in-ear earbud include an on-the-ear headphone and an over-the-ear headphone. The against-the-ear audio device 1 is shown in use, by its user (who may also be referred to as a listener or a wearer.) The against-the-ear audio device 1 has an against-the-ear acoustic transducer or speaker 2 (arranged and configured to reproduce sound directly into an ear of its user), and may optionally have an external microphone 3 (arranged and configured to receive ambient sound directly) and an internal microphone 4 (arranged and configured to directly receive the sound reproduced by the speaker 2.) These microphones may be integrated in their respective audio device housing. The microphones are not necessary for some of the methods described below (e.g., when estimating sound exposure due to headphone playback.) The internal microphone 4 can be useful in making an accurate measurement of in-ear sound pressure level, SPL. Also, there may be more than one external microphone 3, such as a microphone array integrated within a single housing of the against-the-ear audio device 1, that produces multiple channels (multiple sequences of digital audio frames); any reference here to evaluating the strength of "a" microphone signal is understood to be a more general reference to evaluating the strength of one or more sound pickup channels, e.g., a single output of a single microphone, a multi-channel output of a microphone array, or a single output of a sound pickup beamforming process that receives the multi-channel output from the microphone array.

The methods described below are suitable for processing a digital output audio signal that is otherwise essentially ready to drive the speaker 2. The output audio is the result of an audio rendering process that may begin with obtaining an input audio signal via a wired or wireless communication interface, e.g., from a streaming music or podcast or movie service over the Internet. The methods described below as well as the audio rendering process and even the communication interface that delivers the input audio are performed by various electronic hardware components all of which may be integrated in a housing of the against-the-ear device 1. Thus, in instances where the housing of the against-the-ear device 1 has sufficient space and electrical power (e.g., from a rechargeable battery), all of the electronics that obtain, process and produce the transducer signal that drives the speaker 2 can be placed in the same housing. The electronics may include an audio amplifier to drive the speaker 2 with the output audio signal, an optional microphone sensing circuit or amplifier that receives the optional microphone signals converts them into a desired format for digital signal processing, and one or more digital processors (referred to here as "a processor") and memory (e.g., solid state electronic data storage circuitry) where the memory stores instructions for configuring the processor (e.g., instructions to be executed by the processor) to perform the digital signal processing tasks discussed below in more detail.

Note that it is also possible that some or essentially all of the electronics referred to below as implementing the acoustic dosimetry techniques reside in another device, separate from the against-the-ear device 1. For instance, in the case of the against-ear-device 1 being a left headphone or right headphone, the headphone may be connected to an audio source device 5 shown in the example of FIG. 1 as a smartphone, via a wired connection (e.g., a computer bus connector that also delivers power, in which case there may be no need for a power source in the headphone housing) or via a wireless connection (e.g., a BLUETOOTH link.) In both cases, the output audio (that contains user content such as a movie sound track, music or the voice of a far-end user during a phone call) has been rendered by one or more processors ("a processor") in the audio source device 5, and much if not all of the processing described below may also be performed by (or at) the processor in the audio source device 5. For example, the instructions that configure or program the processor can be part of operating system software, or they can be part of application software that is running on top of the operating system program, in the audio source device 5. Thus, one or more of the operations in the acoustic dosimetry process may be performed by or at a processor of a smartphone, a smartwatch, a tablet computer, or other audio source device that can communicate with a headset. For example, the headset may be a peripheral device of the audio source device, or the headset and the audio device may be companion devices, e.g., a headphone that can be paired with or configured to be used along with the audio source device and both can be considered personal devices for a particular user in the sense that they are personally configured for a particular user. The audio source device provides user content output audio, over a wired audio link or over a wireless audio link to the headset, for playback through the speakers of the headset. Alternatively, one or more of the operations of the acoustic dosimetry process could be performed by processors in one or both headphone housings of a headset or elsewhere in the headset (provided the headset has sufficient computing resources to do so.)

The acoustic dosimetry process measures or estimates in-ear SPL, e.g., at or near an eardrum reference point, during user content headphone playback. In one aspect, the in-ear SPL is measured as follows. The signal from the internal microphone 4—see FIG. 1—which picks up sound in the ear canal—may be processed into an equivalent SPL, using for example laboratory calibration results that include correction factors, e.g., equalization, to be applied to the microphone signal. This conversion of the microphone signal into in-ear SPL may be performed during headphone playback (sound conversion through the headset worn by the user.) Alternatively, if the internal microphone 4 is not available, then the process flow in FIG. 2 may be used to estimate the in-ear SPL in a "feedforward" fashion.

Figure 2:
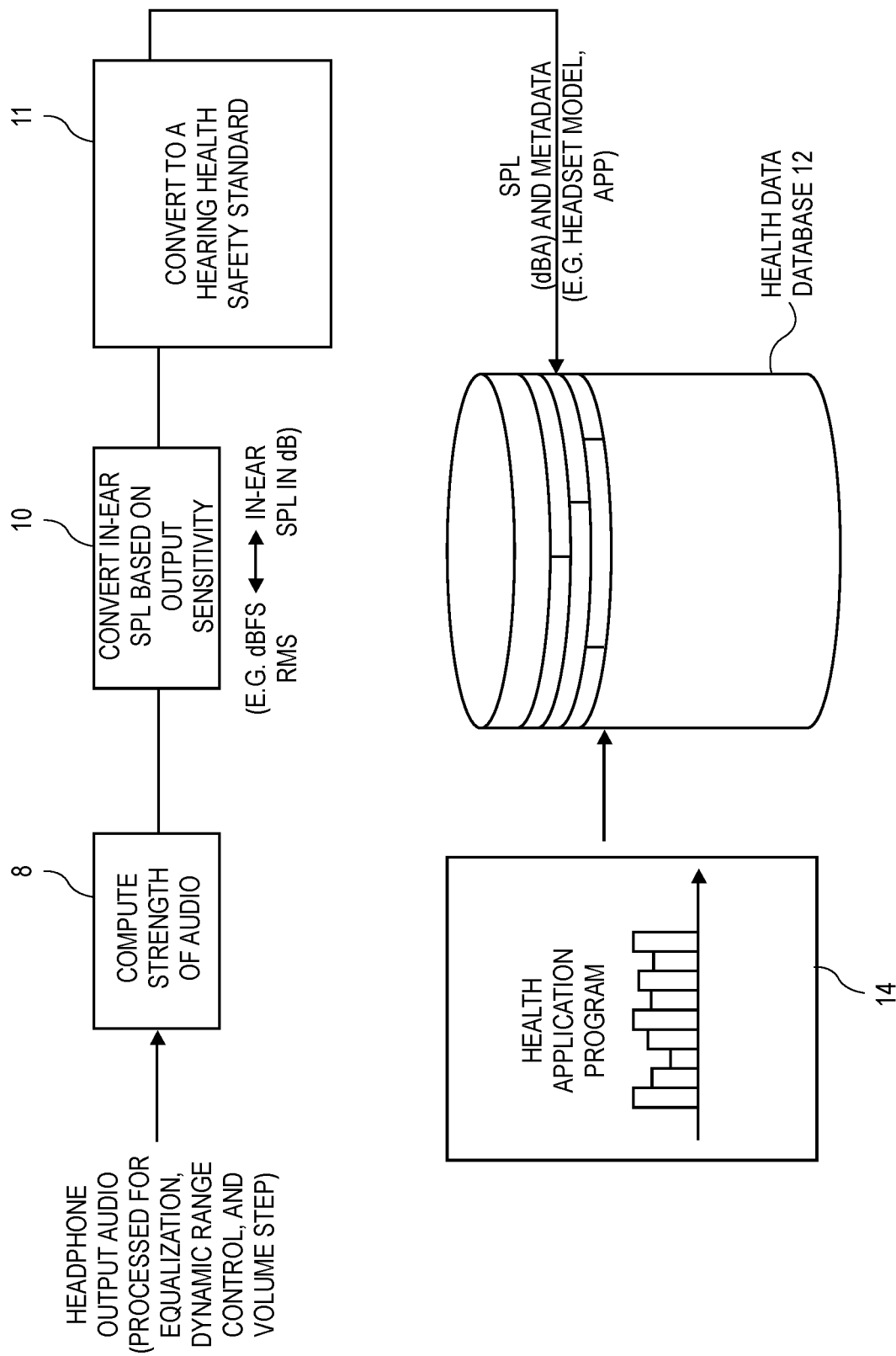
FIG. 2 is a flow diagram of a feedforward type acoustic dosimetry process for headset listening.

Referring to FIG. 2, the process here begins with making laboratory measurements using several different ear simulators and manikins that are wearing a manufactured headset, to produce sound output sensitivity data for different types of ears and ear canals expected in the user population. In one aspect, a nominal set of output sensitivity data is selected for an expected population of users. This factory calibration procedure may be performed on every manufactured headset, for example at production test, or it may be performed once for a group of similar headsets. Statistical techniques may be used to find the best fit for a group of similar headsets, and the best fit is then adopted for a large number of similar headsets. In any case, the calibration procedure assigns sound output sensitivity to each headset. The sound output sensitivity gives a mathematical relationship between strength of the audio signal that is driving the speaker 2 and the strength of the resulting sound output of the speaker 2 as worn by an expected user. It may vary as a function of auditory frequencies of interest, or it may be provided as a statistical measure across an entire audible frequency range, e.g., as relationship between an average input and an average output. It may be stored as a data structure in microelectronic memory within a housing of each headset. In one aspect, the against-the-ear audio device 1 can provide its stored, assigned output sensitivity data, that may include headphone acoustic output sensitivity and volume curve parameters, to an audio source device, for example as described below.

The against-the-ear audio device 1 may then be paired with the separate, audio source device 5 (e.g., as a wireless headset that pairs with a smartphone, a smartwatch, or a tablet computer through a wireless link such as a BLUETOOTH link, or as a wired headset that connects to the audio source device over a wired link such as a serial peripheral bus like a Universal Serial Bus, USB, connection.) A processor in the headset would then receive digital output audio, over the paired connection with the audio source device, and would then drive the audio amplifiers and speakers of the headset to reproduce as sound the output audio (also referred to as a playback signal that contains user content for example media such as music, podcast, video game, or a movie soundtrack.)

The output sensitivity data may be transferred from the memory in the against-the-ear device 1 to memory in the audio source device 5, e.g., over a BLUETOOTH link, where it is used by a processor executing an acoustic dosimetry algorithm or program for headset listening. The process estimates in-ear sound pressure level, SPL, as follows. Staying with FIG. 2, the processor in the audio source device 5 computes a measure of strength of the output audio that is being played back (block 8.) This may be, for example as a root mean square, RMS value. Note that the output audio is a result of an audio rendering process that performs a conventional audio signal processing chain of operations upon an input playback signal (containing media such as music or a movie soundtrack.) These may include dynamic range adjustments, equalization, and gain adjustment for volume step. The processor then converts the RMS value of such output audio into an in-ear SPL, by applying to the RMS value (multiplying it by) the received acoustic output sensitivity data (for the presently used headset.) As an example, dB Full scale RMS values are converted into in-ear SPL dB values. More generally, this is referred to here as a conversion to in-ear SPL, based on output sensitivity (output sensitivity conversion 10.)

Next, in block 11, the measure or estimate of in-ear SPL is converted to units that are suitable for evaluating sound noise exposure (e.g., units specified by a hearing health safety standard which may be a standard or commonly defined metric for permissible sound noise exposure for hearing health.) For example, the in-ear SPL may be multiplied by a transfer function (that has been determined in a laboratory setting) which converts in-ear SPL to an equivalent, free-field or diffuse field measurement of sound as would be picked up by an imaginary reference microphone that is located at some distance away from the user, as defined by the hearing health safety standard. The transfer function may be between a drum reference point, DRP, and a reference microphone. The result of the conversion is referred to here as a computed sound sample, for example in units of SPL dBA (A-weighted decibels).

The sound sample may be computed repeatedly over time, for example every second or other suitable interval during playback, and then accumulated into a batch or sequence of sound samples. The batch is then written into a database 12 of health data stored in memory of the audio source device 5. The database 12 may be secure in the sense that access to it needs to be authorized by the individual user or owner of the health data. In addition to the sound samples, metadata such as the model of the headset that reproduced the output audio as sound, and the application program from which the output audio originated, may also be written as part of the batch. Note here that the sound samples written into the database cannot be used to recover identifying information about the media being played back, e.g., the title of a musical work or of a movie.

The stored or monitored sound samples may then be presented by an application program or app 14 (also being executed by the processor in the audio source device 5) for visualization on a graphical user interface of the audio source device. For example, and still referring to FIG. 2, a health application program as an example of the app 14 may be given authorization to access the locally stored health database 12 to retrieve the sound samples, and computes various statistical measures of the collected sound samples, such as Leq dBA (average) over certain time intervals. The health app may then "show" the user their sound exposure that is due to playback by the against-the-ear audio device 1. The health app may also visualize to the user which portions of the sound samples were produced by which apps (e.g. a music app, a video game app, and a movie player), and which models of against the ear audio devices produced which sound samples. It is expected that the user may use several different models of headsets for listening, such as in-ear wired earbuds, in-ear wireless earbuds, and on-the-ear headphones, at different volume steps or with different media. This useful information may be monitored and reported to the user by the health app. Other ways of reporting useful information to the user about such collected sound samples (acoustic dosimetry) are possible.

Figure 3:
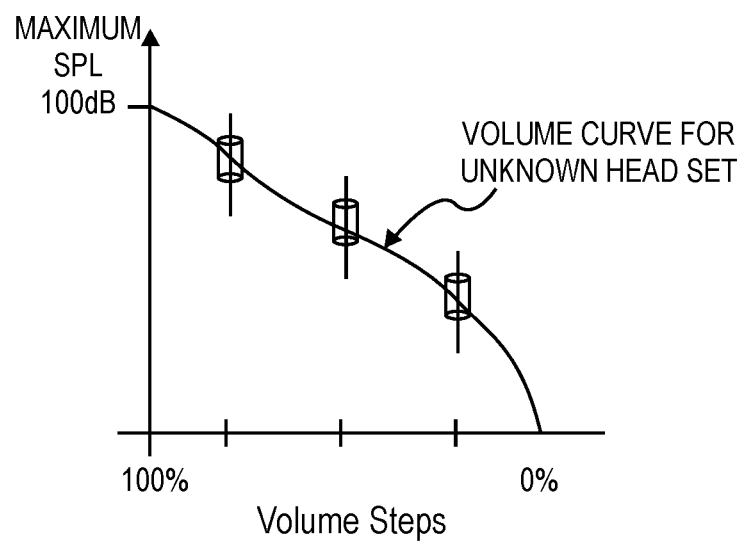
FIG. 3 shows an example volume curve determined for an unknown headset, which relates volume steps to maximum SPL output.

In the case where the factory calibration output sensitivity information is not available, the processor in the audio source device 5 can still detect that an unknown against-the-ear audio device is being used to convert the output audio into sound (e.g., detect that a computer bus connector has been plugged into the audio source device, or a BLUETOOTH link has been established with a headset.) The processor uses that information to select a volume curve. As seen in FIG. 3, a volume curve may be selected, that best fits the characteristics of a number of different types of commercially available headsets (and their published sound output characteristics.) These headsets may have been tested to measure their sound output (e.g., in-ear SPL) versus volume step and while a nominal audio signal processing chain is applied (for example specific to the particular app that is producing the present, output audio in the audio source device). The present volume step (at which the present output audio is being produced) is then applied to the selected volume curve, to obtain an estimate of the maximum SPL at that volume step that is assigned to the connected, unknown headset. A derived output sensitivity relationship between RMS and in-ear SPL is then determined for the unknown headset based on the maximum SPL given by the selected volume curve. The derived output sensitivity relationship is then inserted into the process flow described above and shown in FIG. 2, to compute sound samples in units of SPL dBA (or other units that are suitable for evaluating sound exposure such as per a standard or commonly defined hearing health sound noise exposure calculations.)

It should be noted that the in-ear SPL measurements or estimates as obtained above should be adjusted in cases where there is sound energy being produced by the speaker 2 that comes from other than the playback signal. For instance, the headset may have acoustic noise cancellation, ANC, capability, ambient sound transparency capability (where ambient sound is picked up and actively reproduced during playback, to give the wearer a sense of awareness of her environment), or ambient sound enhancement (where the ambient sound is picked up and amplified when being reproduced so as to compensate for hearing loss or meet a hearing preference of the wearer.) In such cases, the headset may electronically identify such capability during initial pairing with the audio source device, in response to which the acoustic dosimetry process may be configured to adjust its in-ear SPL measurements or estimates accordingly to take into account any such added sound energy. Alternatively, since such additional sound energy is picked up to some extent by the internal microphone 4, it will thus be inherently accounted for in the in-ear SPL measurement made using the signal from the internal microphone 4.

Figure 4:
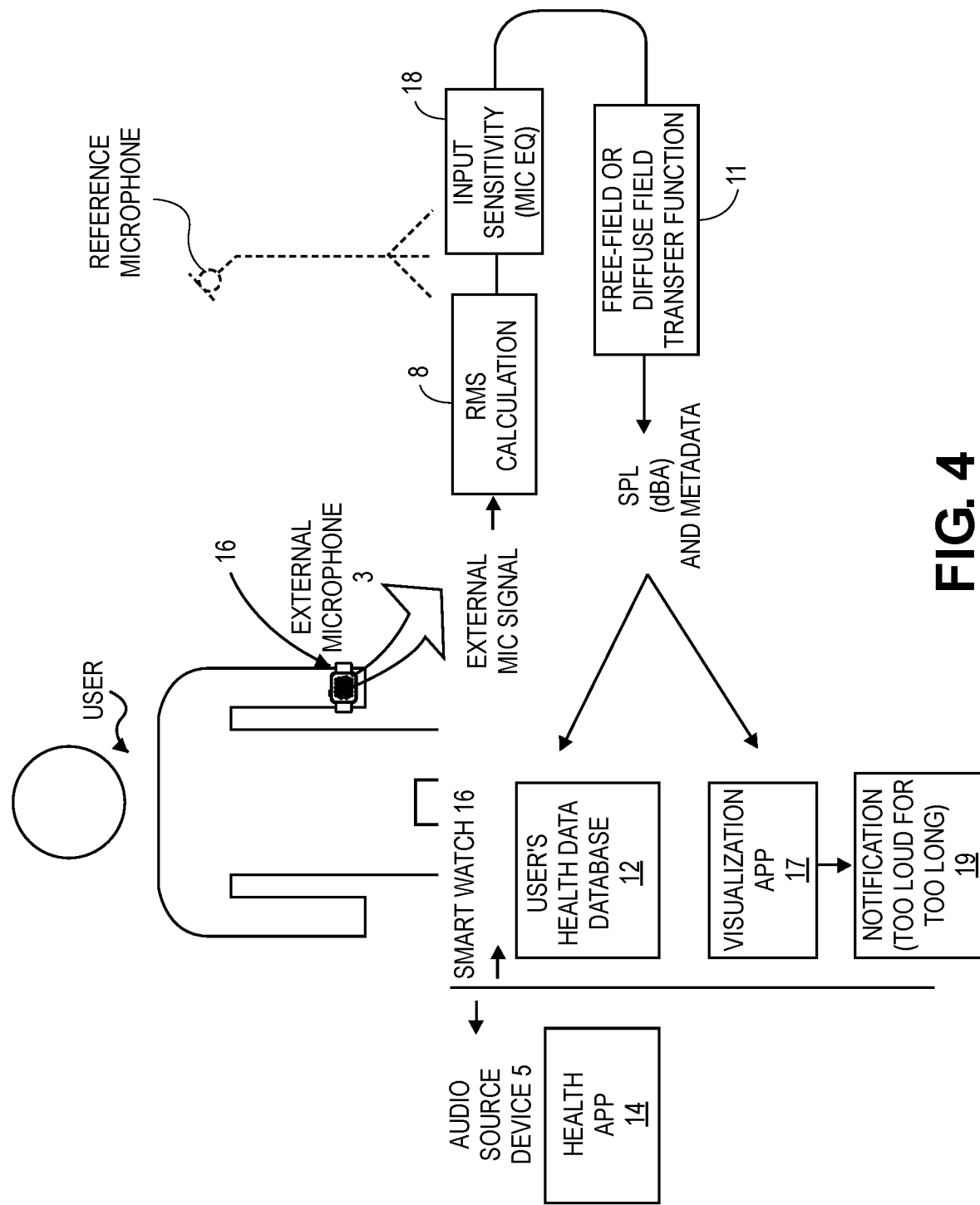
FIG. 4 is a flow diagram of an ambient environment acoustic dosimetry process.

Turning now to FIG. 4, this figure illustrates an example of how to perform acoustic dosimetry of sound that is in the ambient environment of a user (also referred to as environmental sound or noise exposure), e.g., sound from loudspeakers, vehicle sounds, and sound from any other sources in the ambient environment. The external microphone 3 shown in the example of FIG. 1 as being embedded on the outer face of a housing of a headphone and which can as a result perform direct sound pickup in the ambient environment, is now embedded in or integrated in a housing of a smartwatch 16 that is worn around the wrist of the user as shown. The smartwatch 16 may be paired for wireless digital communications with the audio source device 5 (e.g., a smartphone or a tablet computer of the user.) Computations similar to those described above in FIG. 2 that are performed upon the output audio to determine its strength (e.g., RMS) are now performed upon a microphone signal that is generated by an audio device worn by the user. For example, FIG. 4 shows this signal as being generated by the external microphone 3. Note here that there may be more than one external microphone 3, such as a microphone array integrated within a single housing of the audio source device 5 or of the smartwatch 16, that produces multiple channels as multiple sequences of digital audio frames; any reference here to evaluating the strength of "a" microphone signal is understood to be a more general reference to evaluating the strength of one or more sound pickup channels, e.g., a single output of a single microphone, a multi-channel output of a microphone array, or a single output of a sound pickup beamforming process that receives the multi-channel output from the microphone array.

A desired result of ambient environment acoustic dosimetry is to compute a sound sample of the ambient environment, e.g. in units of SPL dBA, by converting the strength of the microphone signal into suitable units for example as defined by a health hearing safety standard. In one aspect, those computations are performed by a low power or auxiliary processor that is integrated in a housing of the smartwatch 16, which helps reduce power consumption (an important goal for the smaller, lower energy density batteries that power the smart watch.) An additional benefit here of having the sound sample computations performed by the low power or auxiliary processor (which also serves to detect a voice trigger phrase in the signal from the external microphone 3) is that the external microphone signal is only buffered for a short time interval, e.g., around one second, and as such does not capture any private conversations that may be present in the ambient environment. The low power or auxiliary processor is one that is continually processing the external microphone signal to detect a voice trigger, while a high power or primary processor in the smart watch is in a low power state (e.g., sleep state.) Once the voice trigger is detected, the high power or primary processor in the smartwatch is transitioned to a high power state (e.g., awake state) in which it can execute the more power intensive tasks of the virtual assistant program.

The process flow of FIG. 4 for ambient/environmental acoustic dosimetry has some differences as compared to the headset acoustic dosimetry or headphone audio exposure given in FIG. 2. These include replacing the user content playback signal with the external microphone signal, replacing the output sensitivity conversion 10 with an input sensitivity conversion 18 (e.g., one that relates dB full scale of the signal produced by the external microphone 3 to SPL that is incident on the external microphone 3) and modifying block 11 to use a free-field or diffuse field transfer function that is between the external microphone 3, instead of the DRP, and the reference microphone of the hearing health safety standard which is depicted in dotted lines in FIG. 4.

The aspects depicted in FIG. 4 also include storage of the health database 12 to which the sound samples are written in batches as described above, within memory of the smartwatch 16 rather than within memory of the audio source device 5. In addition, a visualization application 17 is also being executed by the high power or primary processor in the smartwatch 16, which produces visuals to be displayed on a screen of the smartwatch to the user, showing the levels of ambient sound exposure and their respective durations. The visualization application 17 may also generate a visual or haptic notification 19 in the smartwatch 16, when it determines that the collected sound samples are above a loudness threshold over a time interval threshold (too loud, for too long), which thresholds may be defined by a hearing health safety standard. The notification 19 informs the user that their ambient environment may be too loud for hearing health, and is also referred to here as a "loud environment" notification.

Another aspect of the disclosure here is an "aggregate" acoustic dosimetry process, that may be performed by a programmed digital processor, which estimates the total sound or hearing exposure ("total sound exposure") for a particular user. Computing the total sound exposure is a holistic view in the sense that the processor collects sound measurement inputs from microphones that are in multiple audio devices, respectively, any one of which may be for example within a radius of two meters from the user. Each of the audio devices has a separate housing (containing its respective one or more microphones) and is a different type of device, such as a desktop computer, a laptop computer, a tablet computer, a smartphone, a smartwatch, and a headset. The audio devices may be associated with a particular user, in the sense of how a smartphone, a smartwatch, and a headset are typically described as being "owned by" a particular user (e.g., configured to be personal to the user.) One or more operations of the aggregate acoustic dosimetry process may be performed by a processor of a smartphone, a smartwatch, a tablet computer, or other auto source device that could communicate with the headset. For example, the headset may be a peripheral device of the audio source device, or the headset and the audio device may be companion devices, e.g., a headphone that can be paired with or configured to be used along with the audio source device and both can be considered personal devices for a particular user in the sense that they are personally configured for a particular user. The audio source device provides user content output audio, over a wired audio link or over a wireless audio link to the headset, for playback through the speakers of the headset. Alternatively, one or more of those operations could be performed by processors in one or both headphone housings of a headset or elsewhere in the headset (provided the headset has sufficient computing resources to do so and is able to communicate with other devices of the user to obtain the inputs that are needed by the aggregate dosimetry process.) The aggregate process may interpret the sound measurements using other inputs, referred to here as context inputs which are sources of information that refer to or shed light on the situation in which the user finds themselves (during a given sound measurement.) The total sound exposure is then stored as a time sequence of in-ear SPL values (e.g., in a secure database access to which is authorized by the particular user.) The total sound exposure is thus indicative of the actual sound level to which the user's ear drum has been exposed over a relatively long period of time such as hours, days or weeks.

Figure 5:
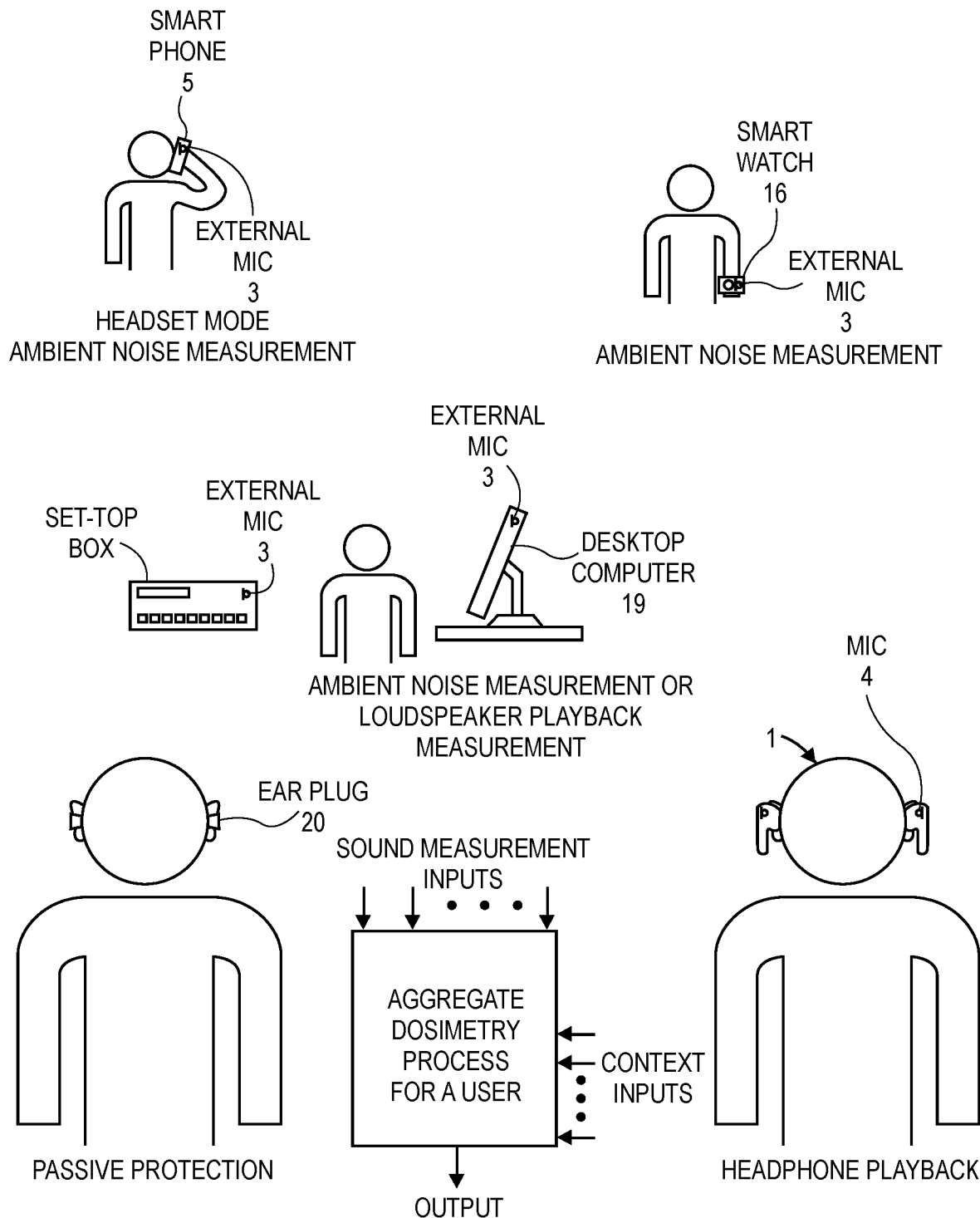
FIG. 5 illustrates an aggregate dosimetry process that receives multiple inputs from different devices.

As seen in FIG. 5 the sound measurement inputs to the aggregate dosimetry process may include two or more of the following that occur at different times while the user is exposed to various sound levels: estimates or measurements of headphone playback sound; sound measurements of environmental noise made by an external microphone 3 that is integrated in the user's smartwatch 16; sound measurements made by an internal microphone 4 that is integrated in an against-ear-audio device 1 such as a headphone that is worn by the user and that may represent either i) headphone playback sound or ii) environmental sound noise that has leaked past the headphone into the user ear, or both; sound measurements of environmental noise made by an external microphone 3 that is integrated in the against-the-ear audio device 1; environmental noise measurements made by an external microphone 3 that is integrated in a smartphone or in another audio source device 5 belonging to the user, for example during a phone call; and sound measurements of environmental noise made by an external microphone 3 of an audio device such as a desktop computer 19 or a lap top computer or a tablet computer. The processor may then convert these diverse sound measurement inputs into a common format, such as in-ear SPL or a hearing health safety standard (see above for example in FIG. 2 and FIG. 4.) The converted or common format SPL values are stored as a time sequence of sound samples, also referred to here as an aggregate dosimetry time sequence that reflects the actual in-ear SPL over time.

As part of the aggregate dosimetry process, the processor may in some cases perform an algorithm that determines which of two or more contemporaneously arriving inputs (e.g., time stamped within the same time interval, or received contemporaneously), will better or more accurately reflect the actual in-ear SPL. In one instance, the input with the highest confidence level is selected while the other contemporaneous inputs are ignored. In other instances, one of the sound measurement inputs is weighted more than the others, before being combined into a single input value (e.g., an estimated in-ear SPL.) For instance, consider the case where a headphone playback estimate, that is based on the current user settable volume at which certain user content such as a movie soundtrack or music is being played back through headphones, is received contemporaneously with an ambient noise measurement; the user in that case is being exposed to various types of sounds at the same time, as they are both listening to music playback on their headphones and are also in a loud ambient environment that could be heard despite the passive attenuation by the worn headset.

The processor stores a time sequence of such estimated, in-ear SPL values that reflects the user's hearing exposure as it varies over time, for example over a period of hours, days or weeks. This time sequence may be analyzed by the processor to determine when the in-ear SPL exceeds a given level threshold over a given time interval, in response to which the processor signals that the "too loud" notification 19 be immediately generated and presented to the user. In general, too loud notifications 14 may be generated in one or more of the user's devices, in response to the estimated in-ear SPL exceeding level thresholds during short term time frames or intervals (e.g., a few seconds) as well as during long term time frames (e.g., an hour, a few hours, a day, a few days, a week.) The too loud notification 14 may for example include a haptic alert on the user's smartwatch 16 or on their smartphone or other audio source device 5. The too loud notification 14 may include in addition to the haptic alert a contemporaneous voice alert (e.g., "consider reducing the volume by two clicks") or an audible alert (e.g., an alarm sound) that may be played back through a speaker of the user's headphone, smartphone, tablet computer, or laptop computer. The too loud notification 14 may also include a contemporaneous visible alert such as a pop-up on a display screen of any one or more of the user's devices.

The time sequence of sound samples (e.g., estimated in-ear SPL values) generated by the aggregate dosimetry process may be tagged (by the processor) with metadata that specifies whether a particular time interval of sound samples is primarily due to headphone playback or primarily due to ambient noise. That time interval and its metadata may be interpreted by the dosimetry process to determine that the user's ambient or environmental noise is exceeding a given level threshold and a given duration threshold, in that particular time interval. Alternatively, the sequence and metadata may be interpreted by the processor to determine that headphone playback is exceeding a given level threshold and a given duration threshold, over a particular time interval. In response, too loud notifications may be signaled in each instance.

The time sequence of sound samples may cover a period of hours, days, or weeks. Location information (as defined by for example global positioning system, GPS, coordinates or other means for defining a geographic location or a place where the user is located) may be associated with or tag the time sequence. When tagged with location information, the time sequence of sound samples may be used by the processor to produce a map of what it determines to be loud locations (e.g., where it has determined that the ambient noise levels and their time durations exceed a hearing health standard.)

Figure 6:
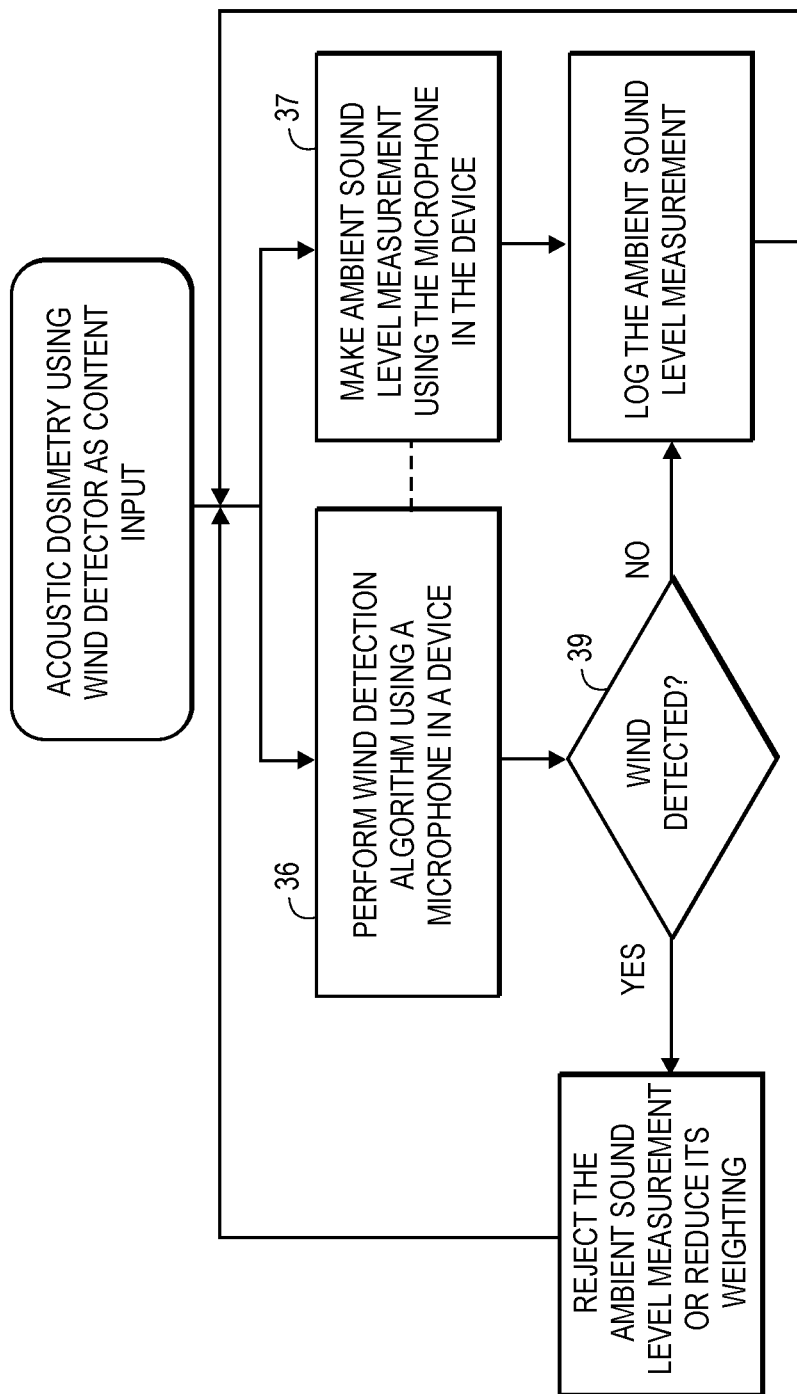
FIG. 6 is a diagram of an acoustic dosimetry process that uses a wind detector as a context input.

In another aspect of the aggregate dosimetry process, the processor determines or logs information on why or how did a loud sound measurement (the in-ear SPL exceeded level and duration thresholds) happen. Such context information may be received as one more context inputs to the process (see FIG. 5.) For example, referring now to FIG. 6, one of the context inputs may be an output of a wind detector (a wind detection algorithm being performed by a digital processor.) In block 36, the wind detector processes each digital audio frame (e.g., 10 msec to 50 msec long) of a received sequence of digital audio frames of a sound pickup channel (e.g., an output of a single microphone, or an output of a sound pickup beamforming process that receives a multi-channel output from a microphone array) to generate an indication such as a confidence level, a binary yes/no, or an estimated wind speed, as to whether a given frequency component in the particular audio frame is due to wind (rather than some ambient sound source.) This context input from the wind detector may then be used by the aggregate dosimetry process to decide, in block 39, whether to log or reject, or alternatively reduce the weight of, a contemporaneously received sound measurement in block 37, as being due to wind (rather than due to a loud sound produced by a sound source in the ambient environment.)

To further ensure accuracy of the computed, total sound exposure, the aggregate acoustic dosimetry process may determine whether or not the user has active and passive hearing protections in place during the sound measurements, and on that basis applies an attenuation or reduction to the sound level measurements. Active hearing protection may be acoustic noise cancellation, ANC, in which a sound transducer (e.g., an earpiece speaker in a headset, a loudspeaker) is being driven to produce anti-noise that is cancelling the ambient noise that would otherwise be heard by the user.

Passive hearing protection may include ear plugs 20 (see FIG. 5), and blockage of the ear due to the against the ear audio device 1 such as a headphone, or due to a smartphone being held against the user's ear, and a result attenuating the ambient noise due to a partial or complete acoustic seal against the ear. In some cases, the processor may have predetermined, stored knowledge of how much to deduct from sound measurements, based on knowledge of the specific type of passive hearing protection being used in a given instance (e.g., sealing type earbuds, loose fitting earbuds, and handset or against the ear usage of a smartphone all of which may be provided by the same entity that is also providing the aggregate dosimetry process.) In other cases, the user may be wearing third party hearing protection whose attenuation effects are unknown to the user and unknown to the provider of the acoustic dosimetry process.

Part of the aggregate dosimetry process may be a process for tracking over time the usage (by a particular user) of passive hearing protection, such as whether or not the user is using passive hearing protection at a concert, and the type of hearing protection such a pair of headphones or a pair of dedicated ear plugs, and what level of attenuation the hearing protection is designed to provide, and logging such usage ever time. This results in a time sequence of attenuation values that can be applied to reduce a synchronized time sequence of environmental and headphone sound exposure measurements, to result in more accurate "net" sound exposure samples. In one instance, the process could prompt the user to manually select from a list of most popular hearing protections, including third party ones that are different than those from the provider of aggregate dosimetry process, the one that they are currently wearing.

A further difficulty in determining the correct amount of passive attenuation is uncertainty in how the hearing protection is physically fitting with the user's ear. For example, the condition of the fit of a headphone or a dedicated ear plug against the user's ear strongly impacts the amount of passive attenuation. When deciding on such an attenuation value, care should be taken to avoid underestimating the sound dose that the user is being exposed to.

Acoustic Dosimetry Based on Processing Touch Images for Rejecting Water Induced Apparent Touches Another one of the inputs to the aggregate dosimetry process in FIG. 5 may be an output of a water event detector (a water detection algorithm being performed by a digital processor.) The water event detector outputs an indication of the presence of water on a particular audio device of the user. That audio device may be, for example, the user's smartwatch that is being worn by the user while the user is in a shower or outside where it is raining, or the user's smartphone or other portable consumer electronics device that is likely to encounter water in the ambient environment. This serves to provide the dosimetry process context for when not to accept, as a valid sample, an ambient sound level measurement made by that audio device. That is because an external acoustic port in the device is likely being struck with water or is continuously covered with water and, as a result, a microphone that is "listening" through that port is likely to generate an erroneous sound level measurement at that point in time.

Figure 7:
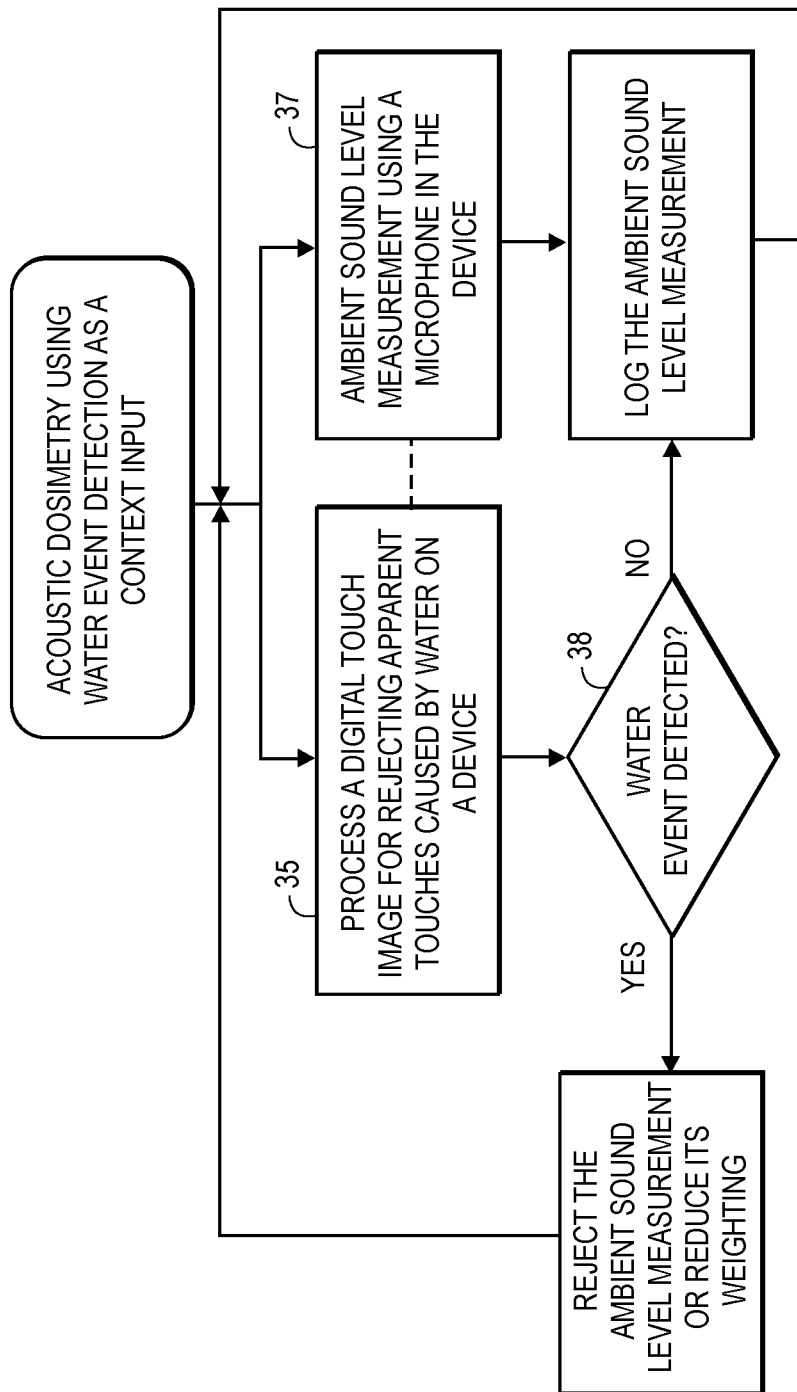
FIG. 7 is a diagram of an acoustic dosimetry process that uses a water event detector as a context input.

Referring now to FIG. 7, this is a flow diagram of a method for acoustic dosimetry in which a water event detector provides a context input. The method may be performed by a digital processor and a touch sensor subsystem within an audio device such as a smartwatch or a smartphone. A digital touch image is acquired from a touch sensitive surface of a touch sensor subsystem (e.g., a touch screen in the device), and is digitally processed for rejecting apparent touches caused by water (block 35.) An ambient sound level measurement is made using a microphone in the device (block 37.) A determination is made as to whether or not the ambient sound level measurement should be logged as a valid sound exposure sample for acoustic dosimetry, or if its weighting should be reduced for when it is combined with other sound measurements inputs (block 38.) This is done based on a result of having processed the touch image, e.g., how much if any of the touch image is determined to be caused by water. In other words, the touch sensing surface in the device is being used to detect water events that become one context for when not to log a measurement of ambient sound level (when using an "open to the ambient" microphone within the audio device.)

In one aspect, processing the touch image includes discriminating between i) floating (or electrically ungrounded) water on the touch sensitive surface and ii) a finger touch (which is electrically grounded.) In another aspect, processing the touch image includes determining there is water on the touch sensitive surface and classifying the determined water on the touch sensitive surface as static (e.g., one or more droplets) or dynamic (e.g., water is flowing like when the device is worn by the user while taking a shower.) In that aspect, the dosimetry process does not log the ambient sound level measurement if the water is classified as dynamic, and does log it if the water is classified as static. In other words, the ambient sound level measurement is logged if the water is classified as static, but not if the water is classified as dynamic.

In yet another aspect, processing the touch includes determining an amount of water on the touch sensitive surface, by for example the processor counting a number of pixels in the touch image. The ambient sound level measurement is not logged if the determined amount of water is greater than a threshold, but is logged if it is less than the threshold. The dosimetry process may then send a loud environment notification to its user, if the logged ambient sound level measurements remain above a threshold for at least a threshold amount of time.

The touch sensitive surface and the microphone may be integrated into a housing of a portable consumer electronics device. In the case where the water event detection process is being performed in a smartwatch (where the touch sensitive surface and perhaps also the microphone is integrated in or part of the smartwatch), a determination of whether or not an ambient sound level measurement is logged is further based on the processor having detected whether or not the smartwatch is on a user's wrist (e.g., by executing an on-wrist detection algorithm.)

A method for acoustic dosimetry in which water events are detected by a processor, and then used as a context input to decide whether or not to log contemporaneous loud sound events, may proceed as follows. A time sequence of touch images is acquired from a touch sensitive surface, and is processed in order to detect floating water on the touch sensitive surface, as a time sequence of water events. Ambient sound level measurements are made using a microphone, as a time sequence, and those are processed to detect loud sounds as a time sequence of loud events. In time intervals over which the time sequence of water events does not correlate with the time sequence of loud events, the loud events are logged for acoustic dosimetry. But in time intervals over which the water events correlate with the loud events, and the water events indicate an amount of floating water that exceeds a threshold or that there is dynamic water (water is flowing across the touch sensitive surface), the loud events are not logged (or they disregarded for purposes of acoustic dosimetry.) For instance, for a time interval during which the water events correlate with contemporaneous loud events, the processor foregoes the presentation of a user notification that indicates exposure to loud sound even though the loud events exceed a level threshold for at least a threshold amount of time. Such water events could indicate an amount of floating water that exceeds a threshold, or they could indicate that there is dynamic water on the touch sensitive surface.

The acoustic dosimetry process may be continuously monitoring the time sequence of logged loud events, and where in response to the logged loud events exceeding a level threshold for at least a threshold amount of time the processor will signal a device of the user, e.g., the user's smartwatch or the user's smartphone, to present a user notification that indicates exposure to loud sound. As suggested above, the user notification may include the display of text or graphics by the touch sensing surface.

Revisiting FIG. 5, the aggregate acoustic dosimetry process is fed a variety inputs some of which are direct sound level measurements while others provide the process with context as why or how a particularly loud sound event is taking place. One such context input discussed above is an output of a wind detector. Another context input that was also discussed above and that may be interpreted to decide not to log an ambient sound level measurement or reduce its weight when combined with other sound level estimates is an output of a water event detector. There may be other context inputs as well, such as the following: a determination that a smartwatch is not on a user's wrist; a determination that a smartwatch environment is windy; and a determination of user context based on accelerometer/gyroscope/magnetic sensor (compass) signals in a smartwatch or in a smartphone, e.g., that the user is walking, running, riding a bicycle, riding in or driving a car. The context inputs may be interpreted by the processor to for example determine that a microphone which is being used to make sound measurements is experiencing high air flow which affects the accuracy of the sound measurement. In addition to sensor-originated context inputs, there may also be manually provided context inputs such as a response by the user to a voice prompt or visual prompt that is asking whether or not the user is in water.

An article of manufacture for headset playback acoustic dosimetry, such as a microelectronic integrated circuit device, may comprise memory having stored therein instructions that configure a processor of an audio source device to perform any one or more of the operations described above.

A digital signal processing method for headset playback acoustic dosimetry at a processor of an audio source device, the method comprising: a) determining in-ear sound pressure level, SPL, that is caused by output audio being converted into sound by a headset worn by a user, wherein the headset is a peripheral device of the audio source device; b) converting the in-ear SPL into a sound sample having units for sound noise exposure; repeating a) and b) a plurality of times to produce a time sequence of sound samples; and writing the time sequence of sound samples to a secure database access to which is authorized by the user. Determining in-ear SPL comprises measuring in-ear SPL from an audio signal produced by an internal microphone of the headset. Determining in-ear SPL comprises: receiving from the headset previously determined acoustic output sensitivity data that is stored in the headset; determining strength of the output audio; and multiplying the acoustic output sensitivity data with the strength of the output audio. The method further comprising writing metadata for the time sequence of sound samples to the database wherein the metadata identifies a model of the headset and an application program from which the output audio originated. The method further comprising executing by the processor in the audio source device an application program that accesses the time sequence of sound samples in the database and computes a statistical measure of the time sequence of sound samples and visualizes the statistical measure through a graphical user interface of the audio source device. The method wherein determining in-ear SPL comprises detecting that the headset is connected to the audio source device but that the output sensitivity data for the connected headset is not available, and in response selecting a volume curve; applying a present volume step to the volume curve to obtain a maximum in-ear SPL; and deriving an output sensitivity relationship based on the maximum in-ear SPL given by the volume curve. The method wherein determining the in-ear SPL accounts for acoustic noise cancelation, ambient sound transparency, or ambient sound enhancement by the headset.

An audio source device with headset playback acoustic dosimetry capability, the audio source device comprising: a processor; and memory having stored therein instructions that configure the processor to a) determine in-ear sound pressure level, SPL, that is caused by output audio being converted into sound by a headset worn by a user, wherein the headset is a peripheral device of the audio source device, b) convert the in-ear SPL into a sound sample having units for sound noise exposure, repeat a) and b) a plurality of times to produce a time sequence of sound samples and write the time sequence of sound samples to a secure database access to which is authorized by the user. The audio source device wherein the processor determines in-ear SPL by measuring in-ear SPL from an audio signal produced by an internal microphone of the headset. The audio source device wherein the processor determines in-ear SPL by: receiving from the headset previously determined acoustic output sensitivity data that is stored in the headset; determining strength of the output audio; and multiplying the acoustic output sensitivity data with the strength of the output audio.

The audio source device wherein the memory has further instructions that configure the processor to write metadata for the time sequence of sound samples to the database wherein the metadata identifies a model of the headset and an application program from which the output audio originated. The audio source device wherein the memory has further instructions that configure the processor to execute an application program that accesses the time sequence of sound samples in the database and computes a statistical measure of the time sequence of sound samples and visualizes the statistical measure through a graphical user interface of the audio source device. The audio source device wherein the processor determines in-ear SPL by: detecting that the headset is connected to the audio source device but that the output sensitivity data for the connected headset is not available, and in response selecting a volume curve; applying a present volume step to the volume curve to obtain a maximum in-ear SPL; and deriving an output sensitivity relationship based on the maximum in-ear SPL given by the volume curve. The audio source device wherein the processor when determining the in-ear SPL accounts for acoustic noise cancelation, ambient sound transparency, or ambient sound enhancement by the headset.

A smartwatch comprising: a smartwatch housing having integrated therein a touch sensitive surface, a microphone, a processor, and memory having stored therein instructions that configure the processor to perform a digital signal processing method for ambient sound acoustic dosimetry in which the processor acquires a touch image from the touch sensitive surface, and processes the touch image for rejecting apparent touches caused by water, makes an ambient sound level measurement using the microphone, contemporaneous with acquiring the touch image; and determines whether or not the ambient sound level measurement is logged as a valid sound exposure sample for acoustic dosimetry, based on processing the touch image. The smartwatch wherein the processor processes the touch image by discriminating between i) floating water on the touch sensitive surface and ii) a finger touch. The smartwatch wherein the processor processes the touch image by: determining there is water on the touch sensitive surface; and classifying the determined water on the touch sensitive surface as static or dynamic. In one aspect, the ambient sound level measurement is not logged if the water is classified as dynamic, and is logged if the water is classified as static. In another aspect, the ambient sound level measurement is logged if the water is classified as static, but not if the water is classified as dynamic. The smartwatch of claim wherein the processor processes the touch image by determining an amount of water on the touch sensitive surface. The smartwatch wherein the processor determines an amount of water by counting a number of pixels in the touch image. The ambient sound level measurement is not logged if the determined amount of water is greater than a threshold. The smartwatch wherein the memory has further instructions that configure the processor to log the ambient sound level measurement if the determined amount of water is less than a threshold.

As described above, one aspect of the present technology is the gathering and use of data available from specific and legitimate sources to monitor sound exposure when using headphones. The present disclosure contemplates that in some instances, this gathered data may include personal information data that uniquely identifies or can be used to identify a specific person. Such personal information data can include demographic data, location-based data, online identifiers, telephone numbers, email addresses, home addresses, data or records relating to a user's health or level of hearing impairment, date of birth, or any other personal information.

The present disclosure recognizes that the use of such personal information data, in the present technology, can be used to the benefit of users. For example, the personal information data can be used to monitor long term exposure to sound to promote hearing health in accordance with their preferences.

The present disclosure contemplates that those entities responsible for the collection, analysis, disclosure, transfer, storage, or other use of such personal information data will comply with well-established privacy policies and/or privacy practices. In particular, such entities would be expected to implement and consistently apply privacy practices that are generally recognized as meeting or exceeding industry or governmental requirements for maintaining the privacy of users. Such information regarding the use of personal data should be prominent and easily accessible by users, and should be updated as the collection and/or use of data changes. Personal information from users should be collected for legitimate uses only. Further, such collection/sharing should occur only after receiving the consent of the users or other legitimate basis specified in applicable law. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations that may serve to impose a higher standard. For instance, in the US, collection of or access to certain health data may be governed by federal and/or state laws, such as the Health Insurance Portability and Accountability Act (HIPAA); whereas health data in other countries may be subject to other regulations and policies and should be handled accordingly.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of the sound exposure processing.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing identifiers, controlling the amount or specificity of data stored (e.g., collecting location data at city level rather than at an address level), controlling how data is stored (e.g., aggregating data across users), and/or other methods such as differential privacy.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting.

What is claimed is:

1. A method for acoustic dosimetry, comprising:
   acquiring a touch image from a touch sensitive surface, and processing the touch image for rejecting apparent touches caused by water;
   making an ambient sound level measurement using a microphone, contemporaneous with acquiring the touch image;
   determining whether or not the ambient sound level measurement is logged as a valid sound exposure sample for acoustic dosimetry, based on processing the touch image; and
   sending a loud environment notification to a user, if logged ambient sound level measurements remain above a threshold for at least a threshold amount of time.

2. The method of claim 1 wherein processing the touch image comprises discriminating between i) floating water on the touch sensitive surface and ii) a finger touch.

3. The method of claim 1 wherein processing the touch image comprises:
   determining there is water on the touch sensitive surface; and
   classifying the determined water on the touch sensitive surface as static or dynamic.

4. The method of claim 3 wherein the ambient sound level measurement is not logged if the water is classified as dynamic, and is logged if the water is classified as static.

5. The method of claim 3 further comprising logging the ambient sound level measurement if the water is classified as static, but not if the water is classified as dynamic.

6. The method of claim 1 wherein processing the touch image comprises determining an amount of water on the touch sensitive surface.

7. The method of claim 6 wherein determining an amount of water comprises counting a number of pixels in the touch image.

8. The method of claim 6 wherein the ambient sound level measurement is not logged if the determined amount of water is greater than a threshold.

9. The method of claim 6 further comprising logging the ambient sound level measurement if the determined amount of water is less than a threshold.

10. The method of claim 1 wherein the touch sensitive surface is part of a smartwatch, and wherein determining whether or not the ambient sound level measurement is logged is further based on detecting whether or not the smartwatch is on a user's wrist.

11. A smartwatch comprising:
a smartwatch housing having integrated therein
   a touch sensitive surface,
   a microphone,
   a processor, and
   memory having stored therein instructions that configure the processor to perform a digital signal processing method for ambient sound acoustic dosimetry in which the processor
      acquires a touch image from the touch sensitive surface, and processes the touch image for rejecting apparent touches caused by water,
      makes an ambient sound level measurement using the microphone, contemporaneous with acquiring the touch image; and
      logging the ambient sound level measurement as a valid sound exposure sample for acoustic dosimetry, based on processing the touch image for rejecting apparent touches caused by water.

12. The smartwatch of claim 11 wherein the processor processes the touch image by discriminating between i) floating water on the touch sensitive surface and ii) a finger touch.

13. The smartwatch of claim 11 wherein the processor processes the touch image by:
   determining there is water on the touch sensitive surface; and
   classifying the determined water on the touch sensitive surface as static or dynamic.

14. The smartwatch of claim 13 wherein the ambient sound level measurement is not logged if the water is classified as dynamic, and is logged if the water is classified as static.

15. The smartwatch of claim 13 wherein the memory has further instructions that configure the processor to log the ambient sound level measurement if the water is classified as static, but not if the water is classified as dynamic.

16. The smartwatch of claim 11 wherein the processor processes the touch image by determining an amount of water on the touch sensitive surface.

17. The smartwatch of claim 16 wherein the processor determines an amount of water by counting a number of pixels in the touch image.

18. The smartwatch of claim 16 wherein the ambient sound level measurement is not logged if the determined amount of water is greater than a threshold.

19. The smartwatch of claim 16 wherein the memory has further instructions that configure the processor to log the ambient sound level measurement if the determined amount of water is less than a threshold.

20. The smartwatch of claim 11 wherein the memory has further instructions that configure the processor to log the ambient sound level measurement based on detecting the smartwatch is on a user's wrist.

* * * * *